United States Patent [19]

Clemence et al.

[11] Patent Number: 4,791,109

[45] Date of Patent: Dec. 13, 1988

[54] NOVEL INDOLE CARBOXAMIDES

[75] Inventors: Francois Clemence; Jacques Guillaume, both of Paris; Gilles Hamon, Montrouge, all of France

[73] Assignee: Roussel Uclaf, Paris, France

[21] Appl. No.: 883,915

[22] Filed: Jul. 10, 1986

[30] Foreign Application Priority Data

Jul. 11, 1985 [FR] France .................. 85 10648

[51] Int. Cl.[4] .................. A61K 31/535; A61K 31/40; C07D 413/12; C07D 209/34
[52] U.S. Cl. .................. 514/235.2; 514/253; 514/323; 514/414; 514/415; 514/418; 544/143; 544/144; 544/373; 546/201; 548/467; 548/486; 548/503; 548/510
[58] Field of Search .............. 548/486, 503, 510, 467; 544/143, 144, 373; 546/201; 514/418, 415, 414, 234, 253, 323, 235.2

[56] References Cited

U.S. PATENT DOCUMENTS

| | | | |
|---|---|---|---|
| 4,313,947 | 2/1982 | Nakagawa et al. | 514/253 |
| 4,333,951 | 6/1982 | Walsh | 514/567 |
| 4,361,562 | 11/1982 | Berthold | 514/253 |
| 4,387,100 | 6/1983 | Machin | 514/383 |
| 4,581,355 | 4/1986 | Tahara et al. | 548/467 |

FOREIGN PATENT DOCUMENTS 89426 9/1983 European Pat. Off. .

Primary Examiner—Mary E. Ceperley
Attorney, Agent, or Firm—Bierman and Muserlian

[57] ABSTRACT

Novel indole-carboxamides of the formula

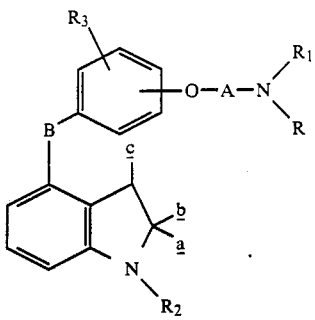

wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, —$CF_3$, $CH_3S$—, —$NH_2$ and —$NO_2$ or $R_1$ and R taken together with the nitrogen atom form an optionally unsaturated heterocycle optionally containing a member of the group consisting of —O—, —S— and

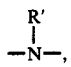

R' is selected from the group consisting of hydrogen, alkyl of 1 to 5 carbon atoms, phenyl, naphthyl, aralkyl of 7 to 12 carbon atoms and substituted phenyl, $R_3$ is selected from the group consisting of hydrogen, alkyl of 1 to 5 carbon atoms, alkoxy of 1 to 3 carbon atoms, chlorine, bromine, iodine, —$NO_2$, —$NH_2$, acylamide of an aliphatic carboxylic acid of 2 to 5 carbon atoms and mono and dialkylamino with alkyl of 1 to 5 carbon atoms, a and b form =O and c is hydrogen or a and c form a carbon-carbon bond and b is hydrogen, A is selected from the group consisting of $(CH_2)_n$— and $$-(CH_2)_m-\underset{\underset{OH}{|}}{CH}-CH_2-,$$

n is an integer from 2 to 5, m is an integer from 1 to 3, B is

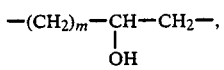

$R_2$ is selected from the group consisting of hydrogen and alkyl of 1 to 5 carbon atoms and their non-toxic, pharmaceutically acceptable acid addition salts having remarkable anti-arrhythmic properties.

31 Claims, No Drawings

NOVEL INDOLE CARBOXAMIDES

STATE OF THE ART

Related indoles are described in copending U.S. patent application Ser. No. 498,835 filed May 27, 1983, now abandoned, Ser. No. 853,030 filed Apr. 17, 1986, and Ser. No. 691,163 filed Jan. 14, 1985, now U.S. Pat. No. 4,650,811, and U.S. Pat. No. 4,333,951 and European Pat. No. 89,426.

OBJECTS OF THE INVENTION

It is an object of the invention to provide the novel indole-carboxamides of formula I and their non-toxic, pharmaceutically acceptable acid addition salts and a novel process for their preparation.

It is another object of the invention to provide novel anti-arrythmic compositions and to a novel method of inducing anti-arrythmic activity in warm-blooded animals.

These and other objects and advantages of the invention will become obvious from the following detailed description.

THE INVENTION

The novel compounds of the invention are selected from the group consisting of indole-carboxamides of the formula

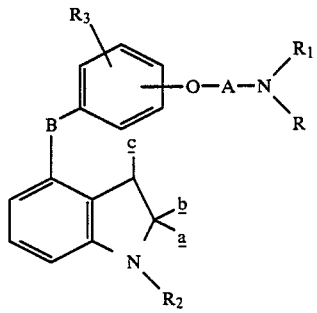

I wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, —$CF_3$, $CH_3S$—, —$NH_2$ and —$NO_2$ or $R_1$ and R taken together with the nitrogen atom form an optionally unsaturated heterocycle optionally containing a member of the group consisting of —O—, —S— and

R' is selected from the group consisting of hydrogen, alkyl of 1 to 5 carbon atoms, phenyl, naphthyl, aralkyl of 7 to 12 carbon atoms and substituted phenyl, $R_3$ is selected from the group consisting of hydrogen, alkyl of 1 to 5 carbon atoms, alkoxy of 1 to 3 carbon atoms, chlorine, bromine, iodine, —$NO_2$, —$NH_2$, acylamide of an aliphatic carboxylic acid of 2 to 5 carbon atoms and mono and dialkylamino with alkyl of 1 to 5 carbon atoms, a and b form =O and c is hydrogen or a and c form a carbon-carbon bond and b is hydrogen, A is selected from the group consisting of —$(CH_2)_n$— and

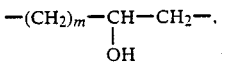

n is an integer from 2 to 5, m is an integer from 1 to 3, B is

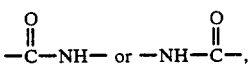

$R_2$ is selected from the group consisting of hydrogen and alkyl of 1 to 5 carbon atoms and their non-toxic, pharmaceutically acceptable acid addition salts.

In the compounds of formula I, examples of linear and branched alkyl are methyl, ethyl, propyl, isopropyl and tert.-butyl. Examples of cycloalkyl of 3 to 7 carbon atoms are cyclopropyl, cyclobutyl, cyclohexyl and preferably cyclopentyl; examples of cycloalkylalkyl are cyclobutylmethyl and preferably cyclopropylmethyl. Examples of aralkyl of 7 to 12 carbon atoms are benzyl and phenethyl optionally substituted with 1 to 3 members of the group consisting of halogen, methyl, ethyl, methoxy, ethoxy, $CF_3$—, $CH_3S$—, —$NH_2$ and —$NO_2$. Examples of heterocycles formed by R and $R_1$ with the nitrogen atom to which they are attached are pyrrolidino, piperidino, morpholino, piperazinyl, methylpiperazinyl, ethylpiperazinyl and propylpiperazinyl. The substituted phenyl may be substituted with the same substituents as benzyl and phenethyl above.

Examples of alkoxy of 1 to 3 carbon atoms are methoxy, ethoxy, propoxy and isopropoxy and examples of aliphatic acyls of 2 to 5 carbon atoms are acetyl and propionyl.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, arylsulfonic acids such as benzene sulfonic acid or p-toluene sulfonic acid and arylcarboxylic acids such as benzoic acid.

Among the preferred compounds of formula I are those wherein $R_2$ is hydrogen, those wherein a and c form a double bond and those wherein $R_3$ is hydrogen, those wherein

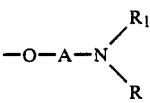

is in the ortho position and those wherein B is

with the —NH— next to the indole side and non-toxic, pharmaceutically acceptable acid addition salts.

Examples of specific preferred compounds of formula I are

2-[-[(1,1-dimethylethyl)amino]ethoxy]-N-(1H-indol-4-yl)benzamide,

2-[3-[(1,1-dimethylethyl)amino]-2-hydroxypropoxy]-N-(1H-indol-4-yl)benzamide,

2-[3-[[bis-(1-methylethyl]amino]-2-hydroxypropoxy]-N-(1H-indol-4-yl)benzamide and 2-[3-[(1,1-dimethylethyl)amino]propoxy]-N-(1H-indol-4-yl)benzamide and their non-toxic, pharmaceutically acceptable acid addition salts.

The novel process of the invention for the preparation of the compounds of formula I comprises reacting a compound of the formula

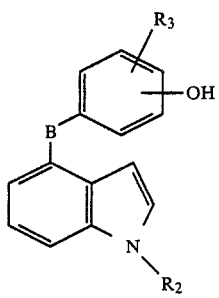

II wherein B, R$_2$ and R$_3$ have the above definitions with a halide of the formula G-Hal  III wherein Hal is chlorine, bromine or iodine and G is selected from the group consisting of —(CH$_2$)$_n$—D and

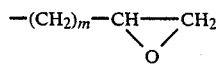

wherein n and m have the above definitions and D is selected from the group consisting of chlorine, bromine, iodine, —OH and and a sulfonate of —OH to obtain a compound of the formula

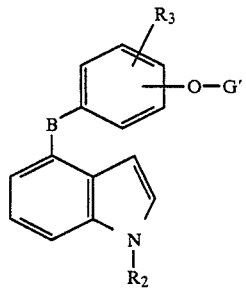

IV wherein B, R$_2$ and R$_3$ have the above definitions and G' is selected from the group consisting of —(CH$_2$)$_n$—Hal and

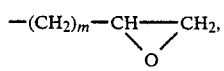

reacting the latter with an amine of the formula

V wherein R and R$_1$ have the above definitions to obtain a compound of the formula

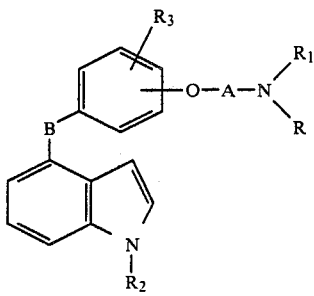

I$_A$ wherein A, B, R, R$_1$, R$_2$ and R$_3$ have the above definitions which may be isolated and/or salified or when one of R and R$_1$ is hydrogen, the latter is subjected to an alkylation reaction or reacted with a halo-genating agent to obtain a compound of the formula

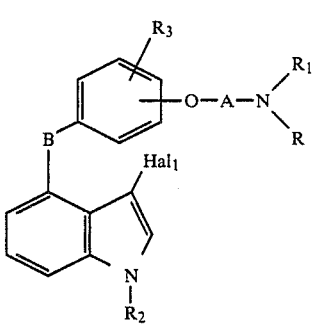

VI wherein Hal$_1$ is a bromine or chlorine and A, B, R, R$_1$, R$_2$ and R$_3$ have the above definitions and subjecting the latter to hydrolysis to obtain a compound of the formula

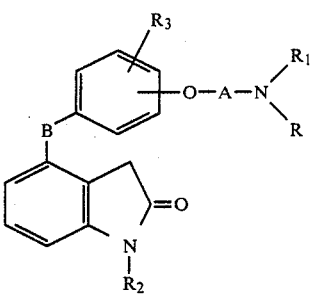

I$_B$ wherein A, B, R, R$_1$, R$_2$ and R$_3$ have the above definitions which is isolated and, if desired, salified.

When A is a chain of the formula —(CH$_2$)$_n$—, a halide of formula III of the formula Hal—(CH$_2$)$_n$—D is used wherein D is chlorine, bromine or iodine and Hal has the above significance. It is preferable that D and Hal should be two different halogens to avoid the condensation of two molecules of the compound of formula IV. Accordingly, for example, when D is a chlorine atom, a more reactive halide such as the bromide will be chosen for Hal.

When a hydroxylated halide of formula III has the formula

HO—(CH$_2$)$_n$—Hal in which n and Hal have the above definitions, it is preferred to operate in the presence of triphenyl phosphine and ethyl azodicarboxylate in tetrahydrofuran.

Advantageously, a sulfonate of this hydroxylated derivative is used, preferably, its tosylate of the formula

TsO—(CH$_2$)$_n$—Hal wherein Ts represents a tosyl radical (4-methylbenzene sulfonate) and n and Hal have the above definitions. The operation is then done by phase transfer, using preferably as the aqueous phase an aqueous solution of an alkaline hydroxide such as potassium hydroxide or sodium hydroxide and as the organic phase non-miscible with water a solvent such as benzene in the presence of a transfer agent such as a quanternary ammonium salt of tetrabutyl ammonium, particularly the bromide or the hydrogenosulfate.

The reaction of the product of formula IV with the amine of formula V is carried out, for example, in an inert organic solvent such as dioxane, benzene, toluene, dimethylformamide, or even an alcohol, preferably ethanol, preferably in the presence of a condensation agent such as an alkali metal carbonate or bicarbonate like potassium carbonate, an alkali metal hydroxide like sodium hydroxide or potassium hydroxide, or a tertiary amine such as triethylamine. The operation can also be done utilizing directly the amine of formula V as solvent.

When A is

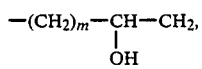

—(CH$_2$)$_m$—CH—CH$_2$,
　　　　　　|
　　　　　　OH a halide is used of the formula

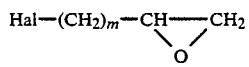

Hal—(CH$_2$)$_m$—CH——CH$_2$
　　　　　　　　\\　／
　　　　　　　　 O and in this case, Hal is preferably chlorine. The reaction of the derivative of formula II with the halide of formula III is then preferably carried out in the presence of a base such as potassium carbonate or sodium carbonate or sodium hydroxide or potassium hydroxide.

The reaction of the compound of formula IV in which G' is

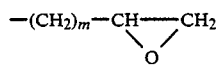

—(CH$_2$)$_m$—CH——CH$_2$
　　　　　　　\\　／
　　　　　　　 O with the amine of formula V is carried out either directly using the amine as solvent, or by using a solvent such as an aliphatic alcohol like methanol or ethanol.

In the product of formula I$_A$, the possible alkylation of the secondary amine of the lateral chain is carried out by the action of an alkyl halide in the presence of an alkali metal carbonate such as sodium or potassium carbonate in an organic solvent. When it is desired to carry out a methylation, it is preferred to use formaldehyde in the presence of a reducing agent such as sodium cyanoborohydride in a solvent such as an aliphatic alcohol such as methanol. Methyl p-toluene sulfonate can also be made to react in the presence of an alkali metal carbonate such as potassium or sodium carbonate in an organic solvent such as xylene.

The halogenation of the derivatives of formulae I$_A$ can be carried out, for example with the brominated complex of pyridine of the formula

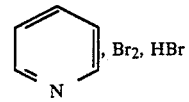

, Br$_2$, HBr in the case of bromination. It is advantageously carried out with a N-halo-succinimide, preferably the N-bromo or the N-chloro-succinimide: the operation is done in dioxane or preferably in acetic acid. The product of formula VI obtained is preferably a chlorinated product.

The hydrolysis of the product of formula VI is carried out, preferably, with a mineral acid such as phosphoric acid, sulfuric acid, or preferably hydrochloric acid in aqueous solution. This solution can be used concentrated, but is preferably diluted for example in normal solution. There can also be used a solvent such as an aliphatic alcohol like ethanol.

The compounds of formula II can be prepared as follows: To obtain a derivative of formula II$_A$

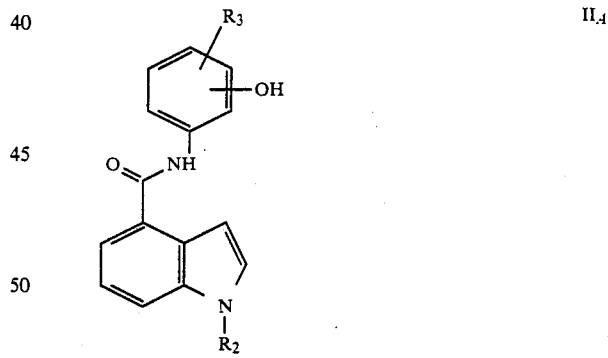

II$_A$ wherein R$_2$ and R$_3$ have the above definition, the corresponding methyl or ethyl indol-4-carboxylate or the corresponding indol-4-carboxylic acid is reacted with a derivative of aminophenol of the formula

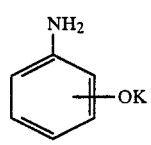

VII wherein K is hydrogen atom or a protective group of the hydroxy to obtain a compound of the formula

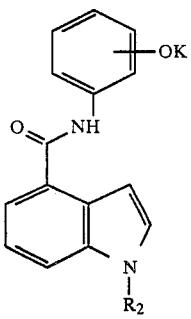

VIII wherein K and R₂ have the above definition wherein if necessary, the hydroxy function is freed to obtain the product of formula II$_A$.

By protective group K of the hydroxy, a benzyl or a tosyl is intended, for example, but preferably tosyl. The reaction of methyl or ethyl indol 4-carboxylate with the derivative of formula VII is preferably carried out in the presence of triisobutylaluminum. The solvent utilized is preferably chloroform and the operation is advantageously carried out at reflux of the reaction mixture.

The reaction of indol-4-carboxylic acid with the derivative of formula VII is carried out in the presence of a dehydrating agent such as carbonyldiimidazole or preferably dicyclohexylcarbodiimide in a solvent such as tetrahydrofuran. The deblocking of the hydroxy of the compound of formula VIII is carried out by hydrogenolysis when K is benzyl, or by saponification when K is tosyl, preferably by means of sodium or potassium hydroxide in a solvent such as a low molecular weight alkanol such as methanol or preferably ethanol.

To obtain a derivative of the formula

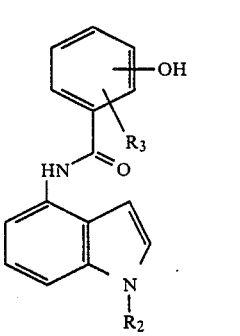

II$_B$ wherein R₂ and R₃ have the above definitions, the corresponding 4-aminoindole is reacted with a methyl or ethyl carboxylate of the phenol or with hydroxy-benzoic acid to obtain the compound of formula II$_B$. When a methyl or ethyl carboxylate of phenol is used, the operation is preferably done in the presence of triisobutylaluminum in a solvent such as chloroform and is done advantageously at reflux of the reaction mixture. When a methyl or ethyl carboxylate of phenol is used, the operation is done under identical conditions to those indicated for the preparation of the compound of formula II$_A$ starting with methyl or ethyl indole-4-carboxylate. When hydroxy-benzoic acid is used, the operation is done in conditions identical to those indicated for the preparation of the compound of formula II starting with indol-4-carboxylic acid.

In a variation of the process for the preparation of the compounds of formula I wherein A is —(CH₂)$_n$—, a derivative of formula II is reacted with a derivative of the formula

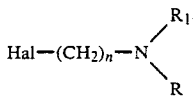

IX wherein Hal, n, R and R₁ have the above definitions to obtain the compound of formula I$_A$ which is converted, if desired, into the corresponding product of formula I$_B$. The derivative of formula IX is reacted in the form of a free amine or, preferably, in the form of a salt like a hydrochloride.

In another variation of process for the preparation of the compounds of formula I wherein R₃ is an optionally substituted amino radical, the derivative in which R₃ is nitro is reduced and, if desired, the amino derivative is reacted with a reactive derivative of the substituent which is intended to be introduced. The corresponding conditions of carrying out are known to one skilled in the art.

The compounds of formula I have a basic character and the addition salts of the compounds of formula I can be prepared advantageously by reacting a mineral or organic acid in essentially stoichiometric proportions with the said derivative of formula I. The salts can be prepared without isolating the corresponding bases.

The novel anti-arrythmic compositions of the invention are comprised of an anti-arrythmically effective amount of at least one compound of formula I and their non-toxic, pharmaceutically acceptable acid addition salts and an inert pharmaceutical carrier or excipient. The compositions may be in the form of tablets, dragees, gelules, capsules, granules, suppositories and injectable solutions or suspensions.

Examples of suitable excipients are talc, arabic gum, lactose, starch, magnesium stearate, cocoa butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of cardiac insufficiency, all forms of angor and for the treatment of arrythmia.

Among the preferred compositions of the invention are those wherein in the active compound a and c form a double bond, those wherein in the active compound R₂ is hydrogen, those wherein R₃ is hydrogen, those wherein

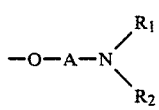

is in the ortho position and those wherein B is

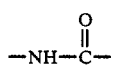

with the —NH—next to the indole and their non-toxic, pharmaceutically acceptable acid additions. Specific preferred compositions are those wherein the active ingredient is 2-[2-[(1,1-dimethylethyl)amino]ethoxy]-N-

(1H-indol-4-yl)benzamide, 2-[3-[(1,1-dimethylethyl)amino]-2-hydroxypropoxy]-N-(1H-indol-4-yl)benzamide, 2-[3-[[bis-(1-methylethyl]amino]-2-hydroxypropoxy]-N-(1H-indol-4-yl)benzamide, 2-[3-[(1,1-dimethylethyl)amino]propoxy]-N-(1H-indol-4-yl)benzamide and their pharmaceutically acceptable acid addition salts.

The novel method of the invention for inducing anti-arrythmic activity in warm-blooded animals, including humans, comprises administering to warm-blooded animals an anti-arrythmically effective amount of at least one compound of formula I and their non-toxic, pharmaceutically acceptable acid addition salts. The compounds may be administered orally, rectally or parenterally and the usual daily dose is 0,65 to 13,5 mg/kg depending on the compound, method of administration and condition treated. For example, the compound of Example 5 may be administered orally at a daily dose of 3 to 12 mg/kg in man for treatment of ventricular, supra-ventricular and junction arrythmia.

The novel intermediates of the invention have the formula

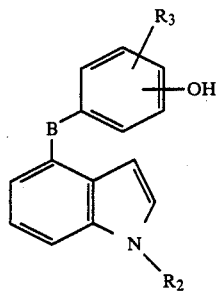

II in which B, $R_2$ and $R_3$ have the above definitions.

In addition to the products described in the examples, the following products constitute new products which are within the scope of the present invention: 2-[3-[(1,1-dimethylpropyl)amino]-2-hydroxypropoxy]-N-(1H-indol-4-yl)benzamide, 2-[3-[(1,1-dimethylethyl)amino]-2-hydroxypropoxy]-N-(1-methyl-1H-indol-4-yl)benzamide and 2-[3-(4-morpholinyl)-2-hydroxypropoxy]-N-(1H-indol-4-yl)benzamide.

In the following examples there are described several preferred embodiments to illustrate the invention. However, it should be understood that the invention is not intended to be limited to the specific embodiments.

EXAMPLE 1

N-[2-[3-[(1,1-dimethylethyl)amino]-2-hydroxypropoxy]-phenyl]-1H-indol-4-carboxamide and its neutral oxalate STEP A: N-[2-[(4-methylphenyl)sulfonyloxy]phenyl]-1H-indol-4-carboxamide 140 ml of triisobutylaluminum in solution in toluene at 1.1 mole/l were added to a solution of 18 g of 2-aminophenol-4-methyl-benzenesulfonate in 300 ml of chloroform, and after stirring for 15 minutes, a solution of 12.15 g of methyl indol-4-carboxylate in 120 ml of chloroform was added. The mixture was refluxed for 20 hours and was then cooled to 0° to −10° C. and 500 ml of an N aqueous solution of hydrochloric acid were added with stirring over 15 minutes. The chloroform phase was then purified by chromatography over silica (eluent: methylene chloride) to obtain 25 g of N-[2-[(4-methylphenyl)sulfonyloxy]phenyl]-1H-indol-4-carboxamide melting at 135° C.

STEP B: N-(2-hydroxyphenyl)-1H-indol-4-carboxamide 250 ml of a solution of potassium hydroxide in ethanol at 10 g per 100 ml were added to a suspension of 25 g of N-[2-[(4-methylphenyl)sulfonyloxy]phenyl]-1H-indol-4-carboxamide in 50 ml of ethanol at 95° C. with stirring under an inert atmosphere and the mixture was stirred for 21 hours. 1 liter of iced water was added, and the mixture was acidified with a concentrated aqueous solution of hydrochloric acid, followed by stirring for a further 15 minutes, filtering, drying and triturating at reflux in 1.5 liters of methylene chloride. After concentrating to about 300 ml, filtering and drying at 80° C. under reduced pressure, 13 g of N-(2-hydroxyphenyl)-1H-indol-4-carboxamide melting at ≈208° C. were obtained.

| U.V. Spectrum (ethanol): | | |
|---|---|---|
| Max. at 230 nm | $E_1^1 = 1,012$ | $\epsilon = 25,500$ |
| Infl. at 265 nm | $E_1^1 = 208$ | |
| Max. at 304 nm | $E_1^1 = 564$ | $\epsilon = 14,200$ |
| Infl. at 318 nm | $E_1^1 = 482$ | |

STEP C: N-[2-[(2-oxiranyl)methoxy]phenyl]-1H-indol-4-carboxamide

Under an inert atmosphere, a solution of 3 g of N-(2-hydroxyphenyl)-1H-indol-4-carboxamide and 1.65 g of potassium carbonate in 100 ml of acetone was refluxed for 24 hours with 4.7 ml of epichlorhydrin and after purifying by chromatography over silica (eluent: ethyl acetate—triethylamine, 9-1) and evaporating to dryness, the residue was triturated in pentane, then filtered and dried under reduced pressure at 60° C. to obtain 2.8 g of N-[2-[(2-oxiranyl)methoxy]phenyl]-1H-indol-4-carboxamide melting at 122° C.

STEP D: N-[2-[3-[(1,1-dimethylethyl)amino]-2-hydroxypropoxy]phenyl]-1H-indol-4-carboxamide A solution of 2.8 g of the product from Step C for 1 hour in 40 ml of ethanol and 7.6 ml of tert-butylamine was heated at 80° C. under an inert atmosphere with stirring and after purification by chromatography over silica (eluent: ethyl acetate—triethylamine, 9-1, then chloroform-methanol 5—5), 3.05 g of N-[2-[3-[(1,1-dimethylethyl)amino]-2-hydroxypropoxy]phenyl-1H-indol-4-carboxamide were obtained (amorphous beige-colored powder).

2.9 g of said product dissolved in 300 ml of acetone was admixed with 480 mg of oxalic acid and the mixture was refluxed for 15 minutes. After concentration to about 200 ml, cooling, filtering and drying under reduced pressure at 80° C.; 2.9 g of the oxalate product were obtained, and 2.35 g after crystallization from methanol melted at ≈200° C.

EXAMPLE 2

N-[2-[2-[(1,1-dimethylethyl)amino]ethoxy]phenyl]-1H-indol-4-carboxamide and its hydrochloride STEP A: N-[2-(2-chloroethoxy)phenyl]-1H-indol-4-carboxamide 2.5 g of N-(2-hydroxyphenyl)-1H-indol-4-carboxamide in 100 ml of benzene and 50 ml of acetonitrile with 850 mg of n-tetra-butylammonium hydrogensulfate, 3.6 ml of 3-chloroethyl p-toluene sulfonate and 50 ml of 5N sodium hydroxide were heated with stirring at 60° C. under an inert atmosphere. After cooling and decanting and extraction with ethyl acetate, the extracts were purified by chromatography over silica (eluent: dichloroethane). Evaporation to dryness under reduced pressure at 50° C. yielded 1.65 g of N-[2-(2-chloroethoxy)phenyl]-1H-indol-4-carboxamide melting at ≃135° C.

STEP B: N-[2-[2-[(1,1-dimethylethyl)amino]ethoxy]phenyl]-1H-indol-4-carboxamide

With stirring at a pressure of 2 bars, a solution of 2.3 g of the product from Step A in 40 ml of ethanol and 37.5 ml of tert-butylamine was heated at 120° C. for 24 hours. After dilution with 400 ml of water and 400 ml of ethyl acetate, the solution was alkalized with sodium hydroxide and saturated with potassium carbonate. The mixture was extracted with ethyl acetate and the crystals obtained were triturated with ether to obtain 2.3 g of N-[2-[2-[(1,1-dimethylethyl)amino]ethoxy]phenyl]-1H-indol-4-carboxamide melting at ≃148° C.

Formation of the hydrochloride

The said base was dissolved in 200 ml of ethyl acetate and a solution of hydrogen chloride in ethyl acetate was added until the pH was acidic. The mixture was refluxed for 15 minutes and after concentrating to about 100 ml, cooling, filtering, drying at 80° C. under reduced pressure and crystallizing from isopropanol, 2.15 g of N-[2-[2-[(1,1-dimethylethyl)amino]ethoxy]phenyl]-1H-indol-4-carboxamide hydrochloride melting at ≃260° C. were obtained.

| U.V. Spectrum (ethanol): | | |
|---|---|---|
| Max. at 229 nm | $E_1^1 = 724$ | $\epsilon = 28,100$ |
| Max. at 302 nm | $E_1^1 = 303$ | $\epsilon = 11,750$ |

EXAMPLE 3

N-[2-[3-[(1,1-dimethylethyl)amino]propoxy]phenyl]-1H-indol-4-carboxamide hydrochloride STEP A: N-[2-(3-chloropropoxy)phenyl]-1H-indol-4-carboxamide A solution of 2 g of N-(2-hydroxyphenyl)-1H-indol-4-carboxamide, 150 ml of tetrahydrofuran, 0.65 ml of 3-chloropropanol and 2.1 g of triphenylphosphine was prepared with stirring under an inert atmosphere and then slowly 1.2 ml of ethyl azodicarboxylate were added. The mixture was stirred for 3 hours after which 2.1 g of triphenylphosphine and 0.65 ml of 3-chloropropanol were added. Then, slowly, 1.2 ml of ethyl azodicarboxylate were added and the mixture was stirred for 16 hours. Then the mixture was evaporated to dryness and the residue was purified by chromatography over silica (eluent: methylene chloride). The solution was evaporated to dryness, triturated with isopropyl ether, filtered and dried under reduced pressure to obtain 1.3 g of N-[2-(3-chloropropoxy)phenyl]-1H-indol-4-carboxamide melting at ≃144° C.

STEP B: N-[2-[3-[(1,1-dimethylethyl)amino]propoxy]phenyl]-1H-indol-4-carboxamide hydrochloride 3.1 g of the product of Step A were heated at 100° C. under a pressure of 2 bars with stirring in 60 ml of ethanol and 30 ml of tertbutylamine. After diluting with 200 ml of water, acidifying with a concentrated aqueous solution of hydrochloric acid, filtering and washing with water, then triturating first with ether then with hot acetone for 15 minutes at reflux, 2.9 g of N-[2-[3-[(1,1-dimethylethyl)amino]propoxy]phenyl]-1H-indol-4-carboxamide hydrochloride melting at ≃238° C. were obtained.

| U.V. Spectrum (ethanol): | | |
|---|---|---|
| Max. at 227 nm | $E_1^1 = 709$ | $\epsilon = 28,400$ |
| Infl. at 262 nm | $E_1^1 = 130$ | |
| Max. at 301 nm | $E_1^1 = 327$ | $\epsilon = 13,100$ |
| Infl. at 320 nm | $E_1^1 = 227$ | |

EXAMPLE 4

2-[3-[(1,1-dimethylethyl)amino]-2-hydroxypropoxy]-N-(1H-indol-4-yl) benzamide and its neutral oxalate STEP A: 2-[N-(1H-indol-4-yl)amido/phenol 92 ml of a 1.1 mole/liter solution of triisobutylaluminum in toluene were added with stirring under an inert atmosphere to a solution of 6.6 g of 4-amino indole in 250 ml of chloroform and then 9.6 ml of methyl salicylate were added. The mixture was refluxed for 20 hours and then cooled to ambient temperature. 300 ml of N hydrochloric acid and 300 ml of methylene chloride were added, followed by washing with water, drying over a desiccant, filtering, evaporating to dryness under reduced pressure at 50° C., triturating with ether, filtering and drying at 60° C. under reduced pressure to obtain 9.4 g of 2-[N-(1H-indol-4-yl)amido]phenol melting at ≃232° C.

| U.V. Spectrum (ethanol): | | |
|---|---|---|
| Infl. at 216 nm | $E_1^1 = 1,595$ | |
| Infl. at 233 nm | $E_1^1 = 680$ | $\epsilon = 17,200$ |
| Infl. at 262 nm | $E_1^1 = 187$ | |
| Infl. at 303 nm | $E_1^1 = 482$ | $\epsilon = 12,200$ |
| Infl. at 314 nm | $E_1^1 = 494$ | $\epsilon = 12,500$ |

Step B: 2-[3-[(1,1-dimethylethyl)amino]-2-hydroxypropoxy]-N-(1H-indol-4-yl)benzamide and its neutral oxalate.

Using the procedure of example 1,3.5 g of 2-[N-(1H-indol-4yl)amido]phenol were reacted to obtain 3 go of the oxalate melting at 190° C.

| U.V. Spectrum (ethanol + HCl 0.1 N): | | |
|---|---|---|
| Infl. at 216 nm | $E_1^1 = 1,003$ | |
| Max. at 296 nm | $E_1^1 = 264$ | $\epsilon = 11,300$ |
| Infl. at 235, 274, 288, 309 nm | | |

EXAMPLE 5

2-[2-[1,1-dimethylethyl)amino]ethoxy]-N-(1H-indol-4-yl)-benzamide hydrochloride

Using the procedure of Example 2, 27 g of 2-[N-(1H-indol-4-yl)-amido]phenolbenzamide were reacted to obtain 4.4 g of 2-[2-[1,1-dimethylethyl)amino]ethoxy]-N-(1H-indol-4-yl)-benzamide hydrochloride melting at ≃248° C.

| U.V. Spectrum (ethanol or ethanol + HCl 0.1 N): | | |
|---|---|---|
| Infl. at 215 nm | $E_1^1 = 1,099$ | $\epsilon = 42,600$ |
| Max. at 293 nm | $E_1^1 = 285$ | $\epsilon = 11,100$ |

EXAMPLE 6

2-[3-[(1,1-dimethylethyl)amino]propoxy]-N-(1H-indol-4-yl)benzamide

Using the procedure of Example 3, 5 g of 2-[N-(1H-indol-4-yl)amido]-phenol benzamide were reacted to obtain 3.1 g of 2-[3-[(1,1-dimethylethyl)amino]propoxy]-N-(1H-indol-4-yl)benzamide melting at ≃146° C., then 3.1 g of its oxalate melting at ≃180° C.

| U.V. Spectrum of the oxalate (ethanol): | | |
|---|---|---|
| Infl. at 218 nm | $E_1^1 = 879$ | |
| Max. at 297 nm | $E_1^1 = 246$ | $\epsilon = 11,200$ |

EXAMPLE 7

N-[2-[2-(1-piperidinyl)ethoxy]phenyl]-1H-indol-4-carboxamide 3 g of N-(2-hydroxyphenyl)-1H-indol-4-carboxamide in 50 ml of benzene, 25 ml of acetonitrile and 50 ml of a 5N aqueous solution of sodium hydroxide were heated to 60° C. for 3 hours with stirring under an inert atmosphere with 0.4 g of 2-tetrabutylammonium hydrogenosulfate and 2.2 g of 2-piperidino-1-chloroethane. After cooling, decanting, extracting with ethyl acetate and purifying by chromatography over silica (eluent: ethyl acetate—triethylamine, 9-1), 3.6 g of N-[2-[2-(1-piperidinyl)ethoxy]phenyl]-1H-indol-4-carboxamide were obtained.

Formation of the fumarate:

The said base was dissolved in 100 ml of isopropanol and 1.15 g of fumaric acid were added. The mixture was refluxed and after cooling, filtering, and taking to dryness under reduced pressure, 3.80 g of the fumarate were obtained in two lots melting at ≃186° C. after crystallization from ethanol.

| U.V. Spectrum: | | |
|---|---|---|
| Infl. at 230 nm | $E_1^1 = 681$ | |
| Infl. at 260 nm | $E_1^1 = 141$ | |
| Max. at 300 nm | $E_1^1 = 271$ | $\epsilon = 13,000$ |
| Infl. at 320 nm | $E_1^1 = 224$ | |

EXAMPLE 8

N-[2-[2-(dimethylamino)ethoxy]phenyl]-1H-indol-4-carboxamide

Using the procedure of Example 7, the hydrochloride of dimethylaminoethyl chloride was reacted to obtain 3.6 g of N-[2-[2-(dimethylamino)ethoxy]phenyl]-1H-indol-4-carboxamide melting at 110° C. then 4.4 g of tartrate (softening point—110° C.)

| U.V. Spectrum of the tartrate (ethanol) | | |
|---|---|---|
| Max. at 228 nm | $E_1^1 = 559$ | $\epsilon = 26,500$ |
| Infl. at 263 nm | $E_1^1 = 123$ | |
| Max. at 300 nm | $E_1^1 = 261$ | $\epsilon = 12,400$ |

EXAMPLE 9

N-[2-[2-[bis(1-methylethyl)amino]ethoxy]phenyl]-1H-indol-4-carboxamide

Using the procedure of Example 7, 8.5 g of the hydrochloride of diisopropylaminoethyl chloride were reacted to obtain 4 g of N-[2-[2-[bis(1-methylethyl)amino]ethoxy]phenyl]-1H-indol-4-carboxamide melting at 145° C. then 2.9 g of the hydrochloride melting at 214° C.

EXAMPLE 10

N-(1H-indol-4-yl)-2-[2-(1-piperidinyl)ethoxy]-benzamide

Using the procedure of Example 7, 2.5 g of 2-[N-(1H-indol-4-yl)amido]phenol and 1.84 g of 2-piperidine-1-chloroethane hydrochloride were reacted to obtain 3.0 g of N-(1H-indol-4-yl)-2-[2-(1-piperidinyl)ethoxy]-benzamide melting at 154° C. after crystallization from ethyl ether.

Formation of the phosphate 2.7 g of the said base were dissolved in 500 ml of ethanol and 10 ml of a 1M solution of phosphoric acid in ethanol were added. The mixture was heated to reflux and 500 ml of methanol were added. The reaction medium was filtered hot, partially concentrated and then cooled, filtered and dried under reduced pressure at 80° C. After crystallizing from an ethanol-methanol mixture (1—1), 2.4 g of the phosphate product melting 238° C. were obtained.

Analysis: $C_{22}H_{25}N_3O_2 \cdot H_3PO_4$ molecular weight = 461.458. Calculated: %C 57.26; %H 6.12; %N 9.11; %P 6.71. Found: 57.1; 6.2; 9.0; 6.6.

EXAMPLE 11

2-[2-(dimethylamino)ethoxy]-N-(1H-indol-4-yl)benzamide

Using the procedure of Example 7, 2.5 g of 2-[N-(1H-indol-4-yl)amido]phenol and 1.44 g of dimethylaminoethyl chloride hydrochloride were heated for 24 hours to obtain 2.15 g of base melting at 138° C. after crystallization from ethyl ether.

Using the procedure of Example 10, 3.3 g of the said base and replacing the ethanol with isopropanol, 3.5 g of the phosphate product were obtained.

Analysis: $C_{19}H_{21}N_3O_2$, $H_3PO_4$: molecular weight = 421.37. Calculated: %C 54.15; %H 5.70; %N 9.97; %P 7.35. Found: 53.8; 5.8; 9.8; 7.3.

EXAMPLE 12

2-[2-[bis(1-methylethyl)-amino]ethoxy-]N-(1H-indol-4-yl) benzamide

Using the procedure of Example 7, 3.5 g of 2-[N-(1H-indol-4-yl)amido]phenol and 2.8 g of diisopropylaminoethyl chloride hydrochloride were reacted to obtain 5.7 g of crude product which was purified by chromatography over silica (eluent: chloroform-acetone-triethylamine, 6-3-1) and crystallizing from chloroform, then from a mixture of isopropanol and methanol (2-1) to obtain 2.25 g of 2-[2-[bis(1-methylethyl)-amino]ethoxy-N-(1H-indol-4-yl) benzamide melting at 180° C.

Analysis: $C_{23}H_{29}N_3O_2$: molecular weight = 379.48. Calculated: %C 72.79; %H 7.70; %N 11.07. Found: 72.9; 7.9; 10.9.

EXAMPLE 13

2-[2-hydroxy-3-(propylamino)-propoxy]-N-(1H-indol-4-yl) benzamide 3.1 g of 2-[(2-oxiranyl) methoxy]-N-(1H-indol-4-yl) benzamide prepared as in example 4 is heated for 2 hours to reflux in 60 cm3 of ethanol and 8.5 cm3 of n-propylamine. The solvents are eliminated under reduced pressure at 50° C., the residue is chromatographed on silica (eluent: chloroform-methanol 7-3) to obtain 2.8 g of 2-[2-hydroxy-3-(propylamino)-propoxy]-N-(1H-indol-4-yl) benzamide.

1.7 g of the said base were dissolved in 200 ml of isopropanol and 100 ml of methanol at reflux, and 585 mg of oxalic acid were added. After partially concentrating the reaction medium, cooling, filtering and drying under reduced pressure at 80° C., 1.7 g of the oxalate product melting at 110° C. were obtained.

Analysis: $C_{21}H_{25}N_3O_3$, $C_2H_2O_4$; molecular weight=467.487. Calculated: %C 60.39; %H 5.95; %N 9.18. Found: 60.2; 6.0; 9.2.

EXAMPLE 14

N-(1H-indol-4-yl)-2-[2-hydroxy-3-[(1-methylethyl)-amino]propoxy] benzamide

Using the procedure of Example 13, 8.6 ml of isopropylamine were reacted to obtain 2.8 g of N-(1H-indol-4-yl)-2-[2-hydroxy-3-[(1-methylethyl)-amino]-propoxy]benzamide.

Using the procedure of Example 13, 2.8 g of the said base and 960 mg of oxalic acid were reacted to obtain 1.7 g of the neutral oxalate product melting 190° C.

Analysis: $C_{21}H_{25}N_3O_3$, $\frac{1}{2}C_2H_2O_4$: molecular weight=412.469. Calculated: %C 64.06; %H 6.35; %N 10.19. Found: 63.3; 6.5; 10.0.

EXAMPLE 15

2-[3-[[bis(1-methylethyl)]amino]-2-hydroxypropoxy-N-(1H-indol-4-yl) benzamide

Using the procedure of Example 13, 14 ml of diisopropylamine were reacted while maintaining reflux for 5 hours to obtain 4 g of crude product which was chromatographed over silica (eluent: chloroform—ethyl acetate-triethylamine 6-3-1) and crystallized from ethyl acetate to obtain 2.4 g of 2-[3-[[bis(1-methylethyl)-]amino]-2-hydroxypropoxy]-N-(1H-indol-4-yl) benzamide melting at 160° C.

Analysis: $C_{24}H_{31}N_3O_3$; molecular weight=409.533. Calculated: %C 70.39; %H 7.63; %N 10.26. Found: 70.4; 7.8; 10.2.

EXAMPLE 16

2-[3-(diethylamino)-2-hydroxypropoxy]-N-(1H-indol-4-yl) benzamide

Using the procedure of Example 13, 10 ml of diethylamine were reacted to obtain 3 g of 2-[3-(diethylamino)-2-hydroxypropoxy]-N-(1H-indol-4-yl) benzamide.

2.5 g of the said base were dissolved in 65.6 ml of 0.1N hydrochloric acid and 10 ml of methanol were added. The methanol was expelled under reduced pressure and the solution was lyophilized to obtain 2.67 g of the hydrochloride product.

Analysis: $C_{22}H_{27}N_3O_3$ HCl: molecular weight=417.939. Calculated: %C 63.23 %H 6.75; %N 10.05; %Cl 8.48. Found: 62.9; 6.9; 9.9; 8.7.

EXAMPLE 17

2-[3-[(1,1-dimethylethyl)amino]-2-hydroxypropoxy]-N-(1H-indol-4-yl) benzamide benzoate 2 g of the base of Example 4 were dissolved in 200 ml of isopropanol at reflux, and 640 mg of benzoic acid were added. The solution was filtered hot, partially concentrated, cooled and filtered, and the product obtained was dried under reduced pressure at 80° C. After crystallizing from isopropanol, 2.0 g of 2-[3-[(1,1-dimethylethyl)amino]-2-hydroxypropoxy]-N-(1H-indol-4-yl)benzamide benzoate melting at 190° C. were obtained.

Analysis: $C_{22}H_{27}N_3O_3$, $C_7H_6O_2$ Molecular weight=503.603. Calculated: %C 69.17; %H 6.61; %N 8.34. Found: 69.4; 6.7; 8.3;

EXAMPLE 18

2-[3-[(1,1-dimethylethyl)amino]-2-hydroxypropoxy]-N-[2,3-dihydro-2-oxo-1H-indol-4-yl] benzamide and its neutral oxalate STEP A: 2-[3-[(1,1-dimethylethyl)amino]-2-hydroxypropoxy-N-(3-chloro-1H-indol-4-yl) benzamide A mixture of 3.3 g of the base of Example 4, 40 ml of acetic acid and 1.3 g of N-chloro-succinimide were stirred for 1 hour at ambient temperature and under an inert atmosphere. The reaction medium was diluted with water, alkalinized with ammonia and extracted with ethyl acetate. The solvents were eliminated under reduced pressure and the residue was chromatographed over silica (eluent: ethyl acetate—triethylamine, 9-1) to obtain 2.5 g of 2-[3-[(1,1-dimethylethyl)amino]-2-hydroxypropoxy-N-(3-chloro-1H-indol-4-yl) benzamide.

STEP B: 2-[3-[(1,1-dimethylethyl)amino]-2-hydroxypropoxy]-N-[2,3-dihydro-2-oxo-1H-indol-4-yl] benzamide 2.5 g of the product of Step A in 35 ml of ethanol and 70 ml of 1N hydrochloric acid was refluxed for 1 hour and the reaction mixture was diluted with water, alkalinized with sodium hydroxide and extracted with ethyl acetate. After elimination of the solvent under reduced pressure, 2.5 g of crude product were obtained which crystallized spontaneously from a mixture of solvents: chloroform—ethyl acetate—triethylamine (6-3-1) to obtain 1.9 g of 2-[3[(1,1-dimethylethyl)amino]-2-hydroxypropoxy]-N-[2,3-dihydro-2-oxo-1H-indol-4-yl]-benzamide melting at 160° C.

1.9 g of the said base were dissolved in 300 ml of isopropanol and 100 ml of methanol at reflux, and 600 mg of oxalic acid were added. Reflux was maintained for 15 minutes, after which the reaction medium was cooled and partially concentrated. The crude expected product was cooled, filtered and dried under reduced pressure. After crystallizing from a mixture of isopropanol and methanol (1-3), 1.8 g of the oxalate were obtained melting at 234° C.

Analysis: $C_{22}H_{27}N_3O_4$, $\frac{1}{2}C_2H_2O_4$: molecular weight=442.495. Calculated: %C 62.43; %H 6.38; %N 9.50. Found: 62.2; 6.4; 9.3.

EXAMPLE 19

2-[3-(4-methyl-1-piperazinyl)-2-hydroxypropoxy]-N-(1H-indol-4-yl)-benzamide 1.8 g of 2-[(2-oxiranyl)methoxy]-N-(1H-indol-4-yl)-benzamide in 36 ml of ethanol and 6.5 ml of N-methyl piperazine was refluxed for 1 hour and the solvents were eliminated under reduced pressure. The residue was chromatographed over silica (eluent: chloroform-ethanol, 9-1) to obtain 1.77 g of 2-[3-(4-methyl-1-piperazinyl)-2-hydroxypropoxy]-N-(1H-indol-4-yl)-benzamide.

1.7 g of the said base were dissolved in 100 ml of isopropanol and 524 mg of oxalic acid were added. The product obtained was filtered off and dried under reduced pressure at 70° C. After crystallizing from isopropanol, 0.96 g of the oxalate melting at 130° C. (decomposes) were obtained.

Analysis: $C_{23}H_{28}N_4O_3$, $C_2H_2O_4$ molecular weight=498.54. Calculated: %C 60.23; %H 6.07; %N 11.24. Found: 60.3; 6.3; 11.2.

EXAMPLE 20

2-[3-[4-(2-methoxyphenyl)-1-piperazinyl]-2-hydroxypropoxy]-N-(1H-indol-4-yl)-benzamide 1.6 g of 2-[(2-oxiranyl)-methoxyl]-N-(1H-indol-4-yl)]-benzamide in 36 ml of ethanol was refluxed for 4 hours with 1.82 ml of (methoxyphenyl)piperazine and the solvent was eliminated under reduced pressure. The residue was purified by chromatography over silica (eluent: chloroform—ethyl acetate—triethylamine, 6-3-1) to obtain 1.85 g of 2-[3-[4-(2-methoxyphenyl)-1-piperazinyl]-2-hydroxypropoxy]-N-(1H-indol-4-yl)-benzamide.

| U.V. Spectrum (ethanol): | | |
|---|---|---|
| Infl. at 235 nm | $E_1^1 = 449$ | $\epsilon = 22,400$ |
| Max. at 287 nm | $E_1^1 = 222$ | $\epsilon = 11,100$ |
| Infl. at 294 nm | $E_1^1 = 215$ | |
| Infl. at 310 nm | $E_1^1 = 179$ | $\epsilon = 8,900$ |

| IR Spectrum (chloroform): | |
|---|---|
| OH free | $3600\ cm^{-1}$ |
| =C—NH | $3481\ cm^{-1}$–$3373\ cm^{-1}$ |
| \C=O/ | $1661\ cm^{-1}$ |
| C=C + aromatic + amide II | $1623\ cm^{-1}$–$1600\ cm^{-1}$–$1587\ cm^{-1}$ $1538\ cm^{-1}$–$1500\ cm^{-1}$–$1485\ cm^{-1}$ |

EXAMPLE 21

2-[3-[[2-(3,4-dimethoxyphenyl)ethyl]amino]-2-hydroxypropoxy]-N-(1H-indol-4-yl)-benzamide 4 g of 2-[(2-oxiranyl)methoxy]-N-(1H-indol-4-yl)-benzamide in 48 ml of ethanol were refluxed for 1 hour with 6.57 ml of dimethoxyphenyl ethylamine and the solvent was eliminated under reduced pressure. The residue was purified by chromatography over silica (eluent: chloroform—methanol, 9-1) to obtain 4.60 g of 2-[3-[[2-(3,4-dimethoxyphenyl)ethyl]-amino]-2-hydroxypropoxy]-(1H-indol-4-yl)-benzamide.

| U.V. Spectrum (ethanol): | | |
|---|---|---|
| Infl. at 218 nm | $E_1^1 = 921$ | |
| Infl. at 230 nm | $E_1^1 = 528$ | $\epsilon = 25,800$ |
| Max. at 288 nm | $E_1^1 = 222$ | $\epsilon = 10,900$ |
| Max. at 299 nm | $E_1^1 = 211$ | $\epsilon = 10,300$ |
| Infl. at 310 nm | $E_1^1 = 187$ | $\epsilon = 9,150$ |
| IR Spectrum (chloroform): | | |
| secondary amide NH | $3360\ cm^{-1}$ | |
| C=O | $1659\ cm^{-1}$ | |
| amide II | $1534\ cm^{-1}$ | |
| aromatic | $1623\ cm^{-1}$–$1601\ cm^{-1}$–$1587\ cm^{-1}$ | |
| aromatic (CH$_3$O—C$_6$H$_3$(OCH$_3$)—CH$_2$) | $1516\ cm^{-1}$ | |
| methoxy | $2837\ cm^{-1}$ | |

EXAMPLE 22

2-[3-(cyclohexylamino)-2-hydroxypropoxy]-N-(1H-indol-4-yl)-benzamide 2.5 g of 2-[(2-oxiranyl)methoxy]-N-(1H-indol-4-yl)-benzamide in 20 ml of ethanol was refluxed for 2 hours with 1.86 ml of cyclohexylamine and the solvent was eliminated under reduced pressure. The residue was chromatographed over silica (eluent: chloroformmethanol 9-1) to obtain 1.97 g of 2-[3-(cyclohexylamino)-2-hydroxypropoxy]-N-(1H-indol-4-yl)-benzamide

| U.V. Spectrum (ethanol): | | |
|---|---|---|
| Infl. at 216 nm | $E_1^1 = 832$ | |
| Infl. at 234 nm | $E_1^1 = 320$ | |
| Infl. at 270 nm | $E_1^1 = 113$ | |
| Max. at 296 nm | $E_1^1 = 212$ | $\epsilon = 8,650$ |
| Infl. at 304 nm | $E_1^1 = 199$ | |
| IR Spectrum (chloroform): | | |
| NH indole | $3480\ cm^{-1}$ | |
| Amide | $1660\ cm^{-1}$ | |
| Amide II | $1536\ cm^{-1}$ | |
| Aromatics: | $1624\ cm^{-1}$ - $1600\ cm^{-1}$ - $1588\ cm^{-1}$ - $1503\ cm^{-1}$ - $1485\ cm^{-1}$ | |

EXAMPLE 23

4-[3-[(1,1-dimethylethyl)amino]-2-hydroxypropoxy]-N-(1H-indol-4-yl)-benzamide

STEP A: 4-[N-(1H-indol-4-yl)amido]phenol

Under an inert atmosphere, 42 ml of triisobutylaluminum in solution in toluene (1.1M) were added slowly to a solution of 3 g of 4-amino-indole in 100 ml of chloroform and 3.5 g of methyl p-hydroxybenzoate in 50 ml of chloroform were then added, followed by reflux for 24 hours. After cooling, 200 ml of 2N hydrochloric acid were added with stirring for 30 minutes and the precipitate was filtered off, washed with water and dried under reduced pressure at 80° C. to obtain 4.9 g of 4-[N-(1H-indol-4-yl)amido/phenol.

| U.V. Spectrum (ethanol): | | |
|---|---|---|
| Max. at 212 nm | $E_1^1 = 1455$ | $\epsilon = 36,700$ |
| Max. at 256 nm | $E_1^1 = 557$ | $\epsilon = 14,000$ |
| Max. at 277 nm | $E_1^1 = 438$ | $\epsilon = 11,000$ |
| Max. at 284 nm | $E_1^1 = 444$ | $\epsilon = 11,200$ |
| Infl. at 294 nm | $E_1^1 = 432$ | |

STEP B: 4-[(2-oxiranyl)methoxy]-N-(1H-(indol-4-yl)]-benzamide

Using the procedure of Example 1, 5.37 g of 4-[N-(1N-indol-4-yl)amido]phenol and 25.8 ml of epichlorhydrin were reacted and after chromatography over silica (eluent: chloroform—ethyl acetate—triethylamine 6-3-1) and triturating in isopropyl ether, 2.9 g of 4-[(2-oxiranyl)methoxy]-N-(1H-(indol-4-yl)]-benzamide melting at 170° C. were recovered.

STEP C: 4-[3-[(1,1-dimethylethyl)amino]-2-hydroxy-propoxyl]-N-(1H-indol-4-yl)-benzamide Using the procedure of Step B of Example 1, 2.9 g of the product of Step B were reacted to obtain 3.5 g of 4-[3-[(1,1-dimethylethyl)amino]-2-hydroxypropoxy]-N-(1H-indol-4-yl)-benzamide melting at 212° C.

2.9 g of the said base were dissolved in 300 ml of isopropanol at reflux, and 0.88 g of fumaric acid and then 20 ml of methanol were added. Reflux was continued for 30 minutes and the reaction medium was partially concentrated, then cooled and filtered under reduced pressure at 80° C. to obtain 2.3 g of crude product. After crystallization from an ethanol-methanol-water mixture (10-10-1), 1.8 g of the neutral fumarate melting >270° C. were obtained.

Analysis: $C_{22}H_{27}N_3O_2$, ½ $C_4H_4O_4$: molecular weight=439.516. Calculated: %C 65.59; %H 6.65; %N 9.56. Found: 65.3; 6.7; 9.6.

EXAMPLE 24

4-chloro-2-[3-[(1,1-dimethylamino]-2-hydroxypropoxy]-N-(1H-indol-4-yl)-benzamide STEP A: 5-chloro-2-[N-(1H-indol-4-yl)amino]phenol Under an inert atmosphere, a solution of 5.28 g of 4-aminoindole, 100 ml of tetrahydrofuran, 6.9 g of 4-chlorosalicyclic acid and 9.06 g of dicyclohexylacarbodiimide was heated to refluxed and the dicyclohexylurea formed was filtered off. The solvent was expelled under reduced pressure at 50° C. and after chromatography over silica (eluent: chloroform—ethyl acetate, 9-1), the residue was triturated with ether and dried to obtain 5.55 g of 5-chloro-2-[N-(1H-indol-4yl-)amido]phenol melting at 245° C.

Analysis: $C_{15}H_{11}N_2ClO_2$: Molecular weight=286.720.

Calculated: %C 62.84; %H 3.87; %N 9.77; %Cl 12.36. Found: 62.5; 4.0; 9.7; 12.3.

STEP B: 4-chloro-2-[(2-oxiranyl)methoxy]-N-(1H-indol-4-yl)-benzamide

Under an inert atmosphere, a solution of 4.5 g of 5-chloro-2-[N-(1H-indol-4-yl)]amido phenol in 150 ml of acetone was heated to reflux with 2.2 g of potassium carbonate and 12.5 ml of epichlorhydrin and the product crystallized out of the reaction medium. The solvent was eliminated under reduced pressure at 50° C. and the residue was taken up in water, filtered and dried under reduced pressure at 80° C. to obtain 5 g of 4-chloro-2-[(2-oxiranyl)methoxy]-N-(1H-indol-4-yl)-benzamide melting at 194° C.

STEP C: 4-chloro-2-[3-[(1,1-dimethylethylamino]-2-hydroxypropoxy]-N-(1H-indol-4-yl)-benzamide 3 g of the product of Step B was refluxed for 2 hours in 100 ml of ethanol and 7.6 ml of terbutylamine and the solvent was expelled under reduced pressure at 50° C. After chromatography over silica (eluent: chloroform-methanol-triethylamine 8-1-1), 5 g of 4-chloro-2-[-3-[(1,1-dimethylethylamino]-2-hydroxypropoxy]-N-(1H-indol-4-)-benzamide were obtained.

5 g of the said base were dissolved in 300 ml of isopropanol and 300 ml of methanol at reflux and then 1.5 g of oxalic acid were added and heating was maintained for 15 minutes. After partially concentrating, colling, filtering and drying under reduced pressure at 80° C., 4.4 g of the oxalate melting at 254° C. were obtained.

Analysis: $C_{22}H_{26}N_3ClO_3$, ½ $C_2H_2O_4$: molecular weight=460,941. Calculated: %C 59.93; %H 5.90; %N 9.12; %Cl 7.69. Found: 59.9; 6.1; 8.9; 7.6.

EXAMPLE 25

2-[3-[(1,1-dimethylethyl)amino]-2-hydroxypropoxy]-N-(1H-indol-4-yl)-5-methoxy-benzamide STEP A: 4-methoxy-2-[N-(1H-indol-4-yl)amido]phenol Under an inert atmosphere, 3.96 of 4-amino indole in 70 ml of tetrahydrofuran were refluxed with 5 g of 5-methoxy-salicylic acid and 6.18 g of dicyclohexylcarbodiimide. A further 618 mg of dicyclohexcarbodiimide were added and stirring was continued at ambient temperature for 20 hours. After filtering, the solvent was eliminated under reduced pressure at 50° C. and the residue was taken up in 300 ml of ethyl acetate. The organic phase was washed with 2N hydrochloric acid, then with a saturated aqueous solution of sodium chloride, dried, and the solvent was evaporated under reduced pressure at 50° C. to obtain 9.4 g of crude product. It was purified by chromatography over silica (eluent: chloroform—ethyl acetate, 9-1), was triturated in isopropyl ether, filtered and dried to obtain 4.7 g of 4-methoxy-2-[N-(1H-indol-4-yl)amido]phenol melting at 225° C.

STEP B: 5-methoxy-2-[(2-oxiranyl)methoxy]-N-(1H-indol-4-yl)-benzamide

Under an inert atmosphere, 4.5 g of 4-methoxy-2[N-(1H-indol-4-yl)-amido]phenol in 150 ml of acetone was heated to reflux for 20 hours with 2.2 g of potassium carbonate and 12.5 ml of epichlorhydrine. The potassium carbonate was filtered off, the solvent was expelled under reduced pressure at 50° C., and the residue was chromatographed over silica (eluent: chloroform—ethyl acetate, 9-1). 5.4 g of product were collected which was triturated in ether, filtered and dried under reduced pressure to obtain 5 g of the expected product. m.p.=122° C.

STEP C: 2-[3-[(1,1-dimethyl ethyl)amino]-2-hydroxypropoxy]-N-(1H-indol-4-yl)-5-methoxy-benzamide By operating as in Step C of Example 24, using 5 g of the product from Step B above at the start, 4.9 g of the expected product were obtained.

By operating as in Step C of Example 24 at the start from 4.9 g of the base obtained above, 3.2 g of the oxalate were obtained.

m.p.=254° C.

Analysis: $C_{23}H_{29}N_3O_4$, ½ $C_2H_2O_4$: molecular weight=456.523. Calculated: %C 63.14; %H 6.62; %N 9.20. Found: 62.9; 6.7; 9.0.

EXAMPLE 26

2-[3-(cyclohexylmethyl)amino]-2-hydroxypropoxyl]-N-(1H-indol-4-yl)-benzamide

A solution of 2.5 g of 2-[(2-oxiranyl)methoxy]-N-(1H-indol-4-yl)-benzamide in 50 ml of ethanol in the presence of 1.147 g of cyclohexane methylamine was refluxed for 2 hours and 15 minutes and the solvent was evaporated under reduced pressure. The residue was chromatographed over silica (eluent: methylene chloride—methanol, 9-1) to obtain 1.97 g of 2-[3-(cyclohexylmethyl)amino]-2-hydroxypropoxy]-N-(1H-indol-4-yl)-benzamide.

| U.V. Spectrum (ethanol): | | |
| --- | --- | --- |
| Infl. at 215 nm | $E_1^1 = 385$ | |
| Infl. at 234 nm | $E_1^1 = 365$ | |
| Infl. at 269 nm | $E_1^1 = 128$ | |
| Infl. at 292 nm | $E_1^1 = 229$ | |
| Max. at 297 nm | $E_1^1 = 237$ | $\epsilon = 10,000$ |

| U.V. Spectrum (ethanol): | |
|---|---|
| Infl. at 310 nm | $E_1^1 = 211$ |

EXAMPLE 27

2-[3-[[2-(3,4-dimethoxyphenyl)ethyl]methylamino]-2-hydroxypropoxy]-N-(1H-indol-4-yl)-benzamide Under an inert atmosphere, a solution of 0.2 g of 2[3-[[2-(3,4-dimethoxyphenyl)ethyl]amino]-2-hydroxypropoxy]-N-(1H-indol-4-yl)-benzamide in 5 ml of methanol in the presence of 0.1 ml of formaldehyde with 40% of water was admixed with a solution of 26 mg of sodium cyanoborohydride and 27.2 mg of zinc chloride in 5 ml of methanol and the reaction mixture was left for 2 hours at ambient temperature. 5 ml of 0.1N sodium hydroxide were added, and the mixture was extracted with ethyl acetate. The organic phase was washed with water, dried, and the solvents were eliminated under reduced pressure to obtain 0.230 g of crude product. It was purified by chromatography over silica (eluent: chloroform—ethyl acetate—triethylamine, 6-3-1) to obtain 0.150 g of 2-[3-[[2-(3,4-dimethoxyphenyl)ethyl]-methylamino]-2-hydroxypropoxy]-N-(1H-indol-4-yl)-benzamide

| U.V. Spectrum (ethanol): | | |
|---|---|---|
| Infl. at 218 nm | $E_1^1 = 794$ | |
| Infl. at 230 nm | $E_1^1 = 429$ | |
| Max. at 286 nm | $E_1^1 = 181$ | |
| Max. at 298 nm | $E_1^1 = 176$ | $\epsilon = 8,850$ |
| Infl. at 310 nm | $E_1^1 = 158$ | |
| Infl. at 318 nm | $E_1^1 = 147$ | |

PHARMACOLOGICAL STUDY

1. Anti-arrhythmic action in the rat

Male rats weighing 300–350 g were anesthetized intra-peritoneally with 1.20 g/kg of urethane, then tracheotomized and submitted to artificial respiration (40–50 breaths of 3 ml/minute). Needles were implanted subcutaneously so as to record the electro-cardiogram of the rats on the $D_{II}$ derivation signal. The products under test were administered intravenously or orally.

Five minutes after the administration of the product intravenously or 1 hour after administration orally, the jugular vein of the rats was perfused with 10 μg/minute from 0.2 ml of a solution of aconitine, and the time of appearance of disturbances of the cardiac rhythm was noted, (10 μg of aconitine corresponding to a perfusion of 0.2 ml of solution). The results are expressed as a percentage of the extension of the time of appearance of the disturbances of the cardiac rhythm as compared with controls, and as a function of the dose of the product under test. The results appearing in the following table show that the products of the present application are endowed with remarkable anti-arrhythmic properties.

| Product of example | route | Dose in mg/kg | Percentage extension of the time |
|---|---|---|---|
| 1 | IV | 0.25 | +31 |
|  |  | 0.5 | +41 |
|  |  | 1 | +110 |
| 2 | IV | 1 | +6 |
|  |  | 2.5 | +57 |
| 3 | IV | 2.5 | +68 |
| 4 | IV | 0.5 | +17 |
|  |  | 1.0 | +38 |
|  |  | 2.5 | +124 |
|  | PO | 5 | +7 |
|  |  | 10 | +46 |
|  |  | 25 | +81 |
| 5 | IV | 0.25 | +9 |
|  |  | 0.5 | +36 |
|  |  | 1 | +33 |
|  |  | 2.5 | +61 |
|  | PO | 2.5 | +22 |
|  |  | 5 | +32 |
|  |  | 10 | +59 |
| 6 | IV | 1 | +23 |
|  |  | 2.5 | +41 |
|  | PO | 2.5 | +29 |
| 15 | IV | 2.5 | +25.5 |
|  |  | 5 | +56 |

2. Study of the acute toxicity

The lethal doses $LD_0$ of the different compounds tested were evaluated after administration orally to mice. The maximum dose not causing any mortality in 8 days was called the $LD_0$ and the following results were obtained.

| Product of example | $LD_0$ in mg/kg |
|---|---|
| 1 | 80 |
| 2 | 80 |
| 4 | >400 |
| 5 | 60 |
| 6 | 200 |
| 12 | >400 |
| 15 | ≧400 |

Various modifications of the products and methods of the invention may be made without departing from the spirit or scope thereof and it is to be understood that the invention is intended to be limited only as defined in the appended claims.

What we claim is:

1. A compound selected from the group consisting of indole-carboxamides of the formula

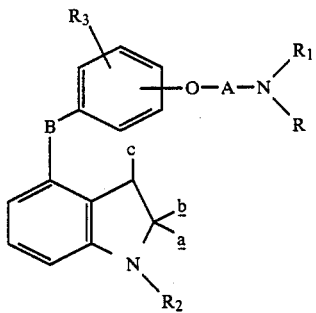

wherein R and $R_1$ are individually selected from the group consisting of hydrogen, alkyl of 1 to 5 carbon atoms, cycloalkyl or 3 to 7 carbon atoms, cycloalkylalkyl of 4 to 7 carbon atoms and aralkyl of 7 to 12 carbon atoms unsubstituted or substituted with 1 to 3 members of the group consisting of halogen, methyl, ethyl, methoxy, ethoxy, —$CF_3$, $CH_2S$—, —$NH_2$ and —$NO_2$ or $R_1$ and R taken together with the nitrogen atom to which they are attached are selected from the group consisting of pyrrolidiino, piperidino, morpholino, piperazinyl, methylpiperazinyl, ethylpiperazinyl, propylpiperazinyl and a phenyl piperazinyl with the phenyl optionally substituted with 1 to 3 members of the group consisting of hydrogen halogen, methyl, ethyl, methoxy, ethoxy, CF₃—, CH₃S—, —NH₂ and —NO₂, R₃ is selected from the group consisting of hydrogen, alkyl of 1 to 5 carbon atoms, alkoxy of 1 to 3 carbon atoms, chlorine, bromine, iodine, —NO₂, —NH₂, acylamide of an aliphatic carboxylic acid of 2 to 5 carbon atoms and mono and dialkylamino with alkyl of 1 to 5 carbon atoms, a and b form =O and c is hydrogen or a and c form a carbon-carbon bond and b is hydrogen, A is selected from the group consisting of —(CH₂)ₙ— and

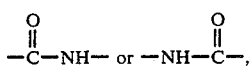

n is an integer from 2 to 5, m is an integer from 1 to 3, B is

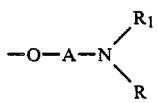

R₂ is selected from the group consisting of hydrogen and alkyl of 1 to 5 carbon atoms and non-toxic, pharmaceutically acceptable acid addition salts thereof.

2. A compound of claim 1 wherein R₂ is hydrogen.
3. A compound of claim 2 wherein a and c form a carbon-carbon bond.
4. A compound of claim 1 wherein R₃ is hydrogen.
5. A compound of claim 1 wherein

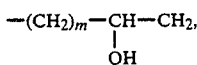

is in the ortho position with respect to B.
6. A compound of claim 1 wherein B is

with NH next to the indole.
7. A compound of claim 1 selected from the group consisting of 2-[2-[(1,1-dimethylethyl)amino]ethoxy]-N-(1H-indol-4-yl)benzamide, and its non-toxic, pharmaceutically acceptable acid addition salts.
8. A compound of claim 1 selected from the group consisting of [2-[3-(1,1-dimethylethyl)amino]-2-hydroxypropoxy]-N-(1H-indol-4-yl) benzamide, and its non-toxic, pharmaceutically acceptable acid addition salts.
9. A compound of claim 1 selected from the group consisting of 2-[3-[[bis-(1-methylethyl]amino]-2-hydroxypropoxy]-N-(1H-indol-4-yl) benzamide, and its non-toxic, pharmaceutically acceptable acid addition salts.
10. A compound of claim 1 selected from the group consisting of 2-[3-[(1,1-dimethylethyl)amino]propoxy]-N-(1H-indol-4-yl)benzamide, and its non-toxic, pharmaceutically acceptable acid addition salts.
11. A compound of the formula

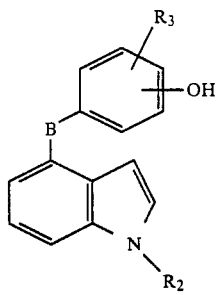

wherein R₂ is selected from the group consisting of hydrogen and alkyl of 1 to 5 carbon atoms, B is —CO—NH— or —NH—CO—, and R₃ is selected from the group consisting of hydrogen, alkyl of 1 to 5 carbon atoms, alkoxy of 1 to 3 carbon atoms, chlorine, bromine, iodine, —NO₂, —NH₂, acylamide of an aliphatic carboxylic acid of 2 to 5 carbon atoms and mono and dialkylamino with alkyl of 1 to 5 carbon atoms.

12. An antiarrythmic composition comprising an antiarrythmically effective amount of at least one compound of claim 1 and an inert pharmaceutical carrier.
13. A composition of claim 12 wherein R₂ is hydrogen.
14. A composition of 13 wherein a and c form a carbon-carbon bond.
15. A compound of claim 12 wherein R₃ is hydrogen.
16. A composition of claim 12 wherein

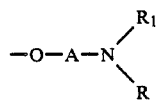

is in the ortho position with repsect to B.
17. A composition of claim 12 wherein B is —NH—CO— with NH next to the indole.
18. A composition of claim 12 wherein the active compound is selected from the group consisting of 2-[2-[(1,1-dimethylethyl)amino]ethoxy]-N-(1H-indol-4-yl)benzamide, and its non-toxic, pharmaceutically acceptable acid addition salts.
19. A composition of claim 12 wherein the active compound is selected from the group consisting of 2-[3-[(1,1-dimethylethyl)amino]2-hydroxypropoxy]-N-(1H-indol-4-yl) benzamide, and its non-toxic, pharmaceutically acceptable acid addition salts.
20. A composition of claim 12 wherein the active compound is selected from the group consisting of 2-[3-[[bis-(1-methylethyl)amino]-2-hydroxypropoxy]-N-(1H-indol-4-yl)-benzamide, and its non-toxic, pharmaceutically acceptable acid addition salts.
21. A composition of claim 12 wherein the active compound is selected from the group consisting of 2-[3-[(1,1-dimethylethyl)amino]propoxy]-N-(1H-indol-4-yl)benzamide, and its non-toxic, pharmaceutically acceptable acid addition salts.
22. A method of inducing antiarrythmic activity in warm-blooded animals comprising administering to warm-blooded animals an antiarrythmically effective amount of at least one compound of claim 1.
23. A method of claim 22 wherein in the active compound R₁ and R₂ are both hydrogen.
24. A method of claim 23 wherein in the active compound a and c form a carbon-carbon bond.

25. A method of claim 22 wherein in the active compound $R_3$ is hydrogen.

26. A method of claim 22 wherein in the active compound

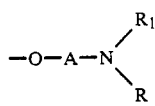

is in the ortho position with respect to B.

27. A method of claim 22 wherein in the active compound B is —NH—CO— with NH next to the indole.

28. A method of claim 24 wherein the active compound is selected from the group consisting of 2-[2-[(1,1-dimethylethyl)amino]ethoxy]-N-(1H-indol-4-yl)benzamide, and its non-toxic, pharmaceutically acceptable acid addition salts.

29. A method of claim 24 wherein the active compound is selected from the group consisting of 2-[3-[(1,1-dimethylethyl)amino]-2-hydroxypropoxy]-N-(1H-indol-4-yl) benzamide, and its non-toxic, pharmaceutically acceptable acid addition salts.

30. A method of claim 24 wherein the active compound is selected from the group consisting of 2-[3[[bis-(1-methylethyl]amino]-2-hydroxypropoxy]-N-(1H-indol-4-yl) benzamide, and its non-toxic, pharmaceuticallly acceptable acid addition salts.

31. A method of claim 24 wherein the active compound is selected from the group consisting of 2-[3-[(1,1-dimethylethyl)amino]propoxy]-N-(1H-indol-4-yl) benzamide, and its non-toxic, pharmaceutically acceptable acid addition salts.

* * * * *